(12) United States Patent
Krishnan et al.

(10) Patent No.: US 10,215,693 B2
(45) Date of Patent: Feb. 26, 2019

(54) INFRARED SPECTROSCOPIC REFLECTOMETER FOR MEASUREMENT OF HIGH ASPECT RATIO STRUCTURES

(71) Applicant: KLA-Tencor Corporation, Milpitas, CA (US)

(72) Inventors: Shankar Krishnan, Santa Clara, CA (US); David Y. Wang, Santa Clara, CA (US)

(73) Assignee: KLA-Tencor Corporation, Milpitas, CA (US)

(*) Notice: Subject to any disclaimer, the term of this patent is extended or adjusted under 35 U.S.C. 154(b) by 0 days.

(21) Appl. No.: 15/382,713

(22) Filed: Dec. 18, 2016

(65) Prior Publication Data

US 2018/0088040 A1 Mar. 29, 2018

Related U.S. Application Data

(60) Provisional application No. 62/401,840, filed on Sep. 29, 2016.

(51) Int. Cl.
*G01B 11/28* (2006.01)
*G01N 21/3563* (2014.01)
(Continued)

(52) U.S. Cl.
CPC ......... *G01N 21/3563* (2013.01); *G01B 11/00* (2013.01); *G01B 11/28* (2013.01);
(Continued)

(58) Field of Classification Search
CPC .......... G01N 21/211; G01N 2021/213; G01N 21/9501; G01N 21/956;
(Continued)

(56) References Cited

U.S. PATENT DOCUMENTS 5,166,752 A 11/1992 Spanier et al.
5,608,526 A 3/1997 Piwonka-Corle et al.
(Continued)

FOREIGN PATENT DOCUMENTS

WO 2007004177 A2 1/2007

OTHER PUBLICATIONS

Gostein et al., "Measuring deep-trench structures with model-based IR," Solid State Technology, vol. 49, No. 3, pp. 38-42, Mar. 1, 2006.
(Continued)

*Primary Examiner* — Michael P Stafira
(74) *Attorney, Agent, or Firm* — Spano Law Group; Joseph S. Spano

(57) ABSTRACT

Methods and systems for performing spectroscopic reflectometry measurements of semiconductor structures at infrared wavelengths are presented herein. In some embodiments measurement wavelengths spanning a range from 750 nanometers to 2,600 nanometers, or greater, are employed. In one aspect, reflectometry measurements are performed at oblique angles to reduce the influence of backside reflections on measurement results. In another aspect, a broad range of infrared wavelengths are detected by a detector that includes multiple photosensitive areas having different sensitivity characteristics. Collected light is linearly dispersed across the surface of the detector according to wavelength. Each different photosensitive area is arranged on the detector to sense a different range of incident wavelengths. In this manner, a broad range of wavelengths are detected with high signal to noise ratio by a single detector.

28 Claims, 10 Drawing Sheets

(51) Int. Cl.
*G01J 3/02* (2006.01)
*G01J 3/28* (2006.01)
*G01N 21/21* (2006.01)
*G01N 21/33* (2006.01)
*G01N 21/47* (2006.01)
*G01B 11/00* (2006.01)
*G01N 21/55* (2014.01)
*G01N 21/31* (2006.01)

(52) U.S. Cl.
CPC ........... *G01J 3/0229* (2013.01); *G01J 3/2803* (2013.01); *G01N 21/211* (2013.01); *G01N 21/33* (2013.01); *G01N 21/47* (2013.01); *G01N 21/55* (2013.01); *G01N 2021/213* (2013.01); *G01N 2021/3137* (2013.01); *G01N 2021/335* (2013.01); *G01N 2021/3568* (2013.01); *G01N 2021/4711* (2013.01)

(58) Field of Classification Search
CPC ... G01N 2201/06113; G01N 2021/214; G01N 2021/8848; G01N 2201/0636; G01N 2201/068; G01N 21/23; G01N 21/55; G01N 2021/212; G01N 2021/95676
See application file for complete search history.

(56) References Cited

U.S. PATENT DOCUMENTS

| | | |
|---|---|---|
| 5,808,738 A | 9/1998 | Garcia-Rubio |
| 5,859,424 A | 1/1999 | Norton et al. |
| 5,877,859 A * | 3/1999 | Aspnes ................ G01J 3/02 250/225 |
| 6,429,943 B1 | 3/2000 | Opsal et al. |
| 6,633,831 B2 | 10/2003 | Nikoonahad et al. |
| 6,734,967 B1 | 5/2004 | Piwonka-Corle et al. |
| 6,816,570 B2 | 10/2004 | Janik et al. |
| 6,859,278 B1 | 2/2005 | Johs et al. |
| 6,895,075 B2 | 5/2005 | Yokhin et al. |
| 6,972,852 B2 | 12/2005 | Opsal et al. |
| 7,026,626 B2 | 4/2006 | Harrison |
| 7,478,019 B2 | 1/2009 | Zangooie et al. |
| 7,755,764 B2 | 7/2010 | Kwak et al. |
| 7,826,071 B2 | 11/2010 | Shchegrov et al. |
| 7,907,264 B1 | 3/2011 | Krishnan |
| 7,929,667 B1 | 4/2011 | Zhuang et al. |
| 7,933,026 B2 | 4/2011 | Opsal et al. |
| 8,009,938 B2 | 8/2011 | Davis et al. |
| 8,860,937 B1 | 10/2014 | Dziura et al. |
| 8,879,073 B2 | 11/2014 | Madsen et al. |
| 9,116,103 B2 | 8/2015 | Wang et al. |
| 9,291,554 B2 | 3/2016 | Kuznetsov et al. |
| 9,310,290 B2 | 4/2016 | Wang et al. |
| 9,915,522 B1 | 3/2018 | Jiang et al. |
| 2012/0250032 A1 | 10/2012 | Wilde et al. |
| 2012/0257213 A1 | 10/2012 | Schnleber |
| 2013/0114085 A1 | 5/2013 | Wang et al. |
| 2013/0222795 A1 | 8/2013 | Madsen et al. |
| 2014/0110582 A1 | 4/2014 | Marx et al. |
| 2014/0111791 A1 | 4/2014 | Manassen et al. |
| 2014/0166862 A1 * | 6/2014 | Flock ................ G01N 21/9501 250/208.2 |
| 2014/0172394 A1 | 6/2014 | Kuznetsov et al. |
| 2014/0222380 A1 | 8/2014 | Kuznetsov et al. |
| 2014/0297211 A1 | 10/2014 | Pandev et al. |
| 2014/0316730 A1 | 10/2014 | Shchegrov et al. |
| 2014/0375981 A1 * | 12/2014 | Wang ................ G01N 21/9501 356/51 |
| 2014/0375983 A1 | 12/2014 | Wolf et al. |
| 2015/0042984 A1 | 2/2015 | Pandev et al. |
| 2015/0046118 A1 | 2/2015 | Pandev et al. |
| 2015/0055123 A1 * | 2/2015 | Rotter ................ G02B 5/3091 356/51 |
| 2015/0193926 A1 | 7/2015 | Berlatzky et al. |
| 2015/0204664 A1 | 7/2015 | Bringoltz et al. |
| 2016/0139032 A1 | 5/2016 | Rampoldi et al. |
| 2016/0161245 A1 | 6/2016 | Fu et al. |
| 2016/0238378 A1 | 8/2016 | Marx |
| 2016/0245741 A1 * | 8/2016 | Krishnan ............. G01J 3/0205 |

OTHER PUBLICATIONS

International Search Report dated Jan. 12, 2018, for PCT Application No. PCT/US2017/053825 filed on Sep. 27, 2017 by KLA-Tencor Corporation, 3 pages.

Ku, Yi-Sha & Yang, Fu Shiang. Reflectometer-based metrology for high-aspect ratio via measurement. Center for Measurement Standards, ITRI Optical Society of America 2010.

* cited by examiner

| | PREDICTED 3-SIGMA MEASUREMENT PRECISION [ANGSTROMS] | | |
|---|---|---|---|
| | ILLUMINATION WAVELENGTHS | a-CARBON FILM 15,000 ANGSTROM THICKNESS | a-CARBON FILM 20,000 ANGSTROM THICKNESS |
| SE | 950-2200 NM | 74 (0.5%) | 500 (2.5%) |
| SE | 950-2500 NM | 65 (0.45%) | 450 (2.25%) |
| SR | 950-2200 NM | 27 (0.2%) | 149.4 (0.75%) |
| SR | 950-2500 NM | 18 (0.15%) | 72 (0.35%) |
165
FIG. 3
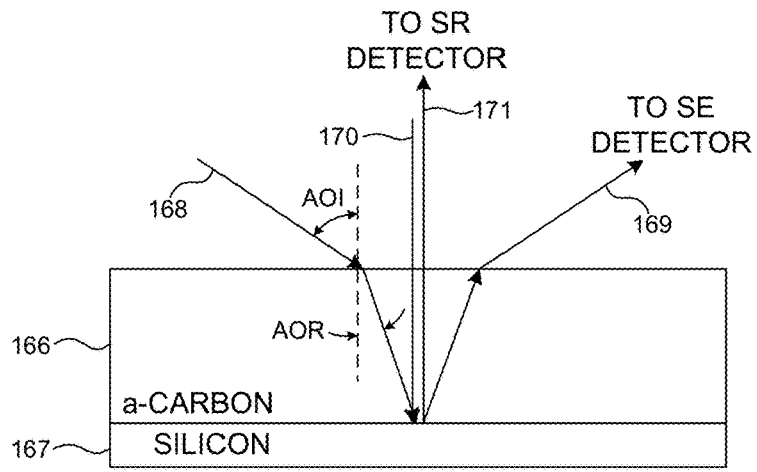
FIG. 4
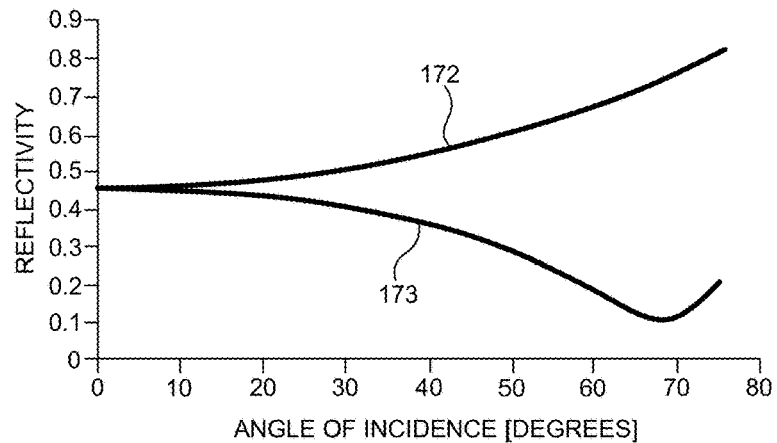
FIG. 5

INFRARED SPECTROSCOPIC REFLECTOMETER FOR MEASUREMENT OF HIGH ASPECT RATIO STRUCTURES

CROSS REFERENCE TO RELATED APPLICATION

The present application for patent claims priority under 35 U.S.C. § 119 from U.S. provisional patent application Ser. No. 62/401,840, filed Sep. 29, 2016, the subject matter of which is incorporated herein by reference in its entirety.

TECHNICAL FIELD

The described embodiments relate to metrology systems and methods, and more particularly to methods and systems for improved measurement of semiconductor structures.

BACKGROUND INFORMATION

Semiconductor devices such as logic and memory devices are typically fabricated by a sequence of processing steps applied to a specimen. The various features and multiple structural levels of the semiconductor devices are formed by these processing steps. For example, lithography among others is one semiconductor fabrication process that involves generating a pattern on a semiconductor wafer. Additional examples of semiconductor fabrication processes include, but are not limited to, chemical-mechanical polishing, etch, deposition, and ion implantation. Multiple semiconductor devices may be fabricated on a single semiconductor wafer and then separated into individual semiconductor devices.

Metrology processes are used at various steps during a semiconductor manufacturing process to detect defects on wafers to promote higher yield. Optical metrology techniques offer the potential for high throughput without the risk of sample destruction. A number of optical metrology based techniques including scatterometry and reflectometry implementations and associated analysis algorithms are commonly used to characterize critical dimensions, film thicknesses, composition, overlay and other parameters of nanoscale structures.

Flash memory architectures are transitioning from two dimensional floating-gate architectures to fully three dimensional geometries. In some examples, film stacks and etched structures are very deep (e.g., up to six micrometers in depth). Such high aspect ratio structures create challenges for film and CD measurements. The ability to measure the critical dimensions that define the shapes of holes and trenches of these structures is critical to achieve desired performance levels and device yield.

Many optical techniques suffer from low signal-to-noise ratios (SNRs), as only a small fraction of the illumination light is able to reach the bottom of high aspect ratio features, and reflect upwards to the detector. Thus, many available high-throughput metrology techniques are unable to reliably perform CD and film measurements of high aspect ratio structures. Critical dimension, small angle X-ray scatterometry (CD-SAXS), normal incidence reflectometry, and scatterometry are being explored as measurement solutions for high aspect ratio structures, but development is still ongoing.

Cross-sectional scanning electron microscopy (SEM) is a low throughput, destructive technique that is not suitable for inline metrology. Atomic force microscopy (AFM) is limited in its ability to measure high aspect ratio structures and has relatively low throughput. CD-SAXS has not yet been demonstrated to achieve high throughput capabilities required by the semiconductor industry. Model based infrared reflectometry (MBIR) has been used for metrology of high aspect ratio DRAM structures, but the technique lacks the resolution provided by shorter wavelengths and the measurement spot sizes are too large for semiconductor metrology. See "Measuring deep-trench structures with model-based IR," by Gostein et al., Solid State Technology, vol. 49, no. 3, Mar. 1, 2006, which is incorporated by reference as if fully set forth herein.

Optical CD metrology currently lacks the ability to measure the detailed profile of structures with micron scale depths and lateral dimensions in a relatively small spot (e.g., less than 50 microns, or even more preferably, less than 30 microns) at high throughput. U.S. Pat. No. 8,860,937, which is incorporated by reference as if fully set forth herein, describes infrared spectroscopic ellipsometry techniques that are suitable for characterization of high aspect ratio structures. However, the described techniques suffer from long measurement times for measurements spanning the ultraviolet and infrared wavelengths, wavelength stability limitations, and limited range of infrared wavelengths during operation.

In summary, ongoing reductions in feature size and increasing depths of structural features impose difficult requirements on optical metrology systems. Optical metrology systems must meet high precision and accuracy requirements for increasingly complex targets at high throughput to remain cost effective. In this context, speed of broadband illumination and data collection, range of infrared wavelengths have emerged as critical, performance limiting issues in the design of optical metrology systems suitable for high aspect ratio structures. Thus, improved metrology systems and methods to overcome these limitations are desired.

SUMMARY

Methods and systems for performing spectroscopic reflectometry measurements of semiconductor structures at infrared wavelengths are presented herein. In some embodiments, spectra including ultraviolet, visible, and infrared wavelengths are simultaneously measured at high throughput with the same alignment conditions. In this manner, machine errors, such as wavelength errors, are uniformly corrected across all measured wavelengths.

In another aspect, the spectroscopic measurements are performed off-axis from the direction normal to the surface of the wafer to reduce the influence of backside reflections on the measurement results.

In yet another aspect, a broad range of infrared wavelengths is detected by a detector that includes multiple photosensitive areas having different sensitivity characteristics. Collected light is linearly dispersed across the surface of the detector according to wavelength. Each different photosensitive area is arranged on the detector to sense a different range of incident wavelengths. In this manner, a broad range of wavelengths are detected with high signal to noise ratio by a single detector. These features, individually, or in combination, enable high throughput measurements of high aspect ratio structures (e.g., structures having depths of one micrometer or more) with high throughput, precision, and accuracy.

In a further aspect, a metrology system incorporating an infrared spectroscopic reflectometer as described herein also includes one or more additional measurement channels operating in the wavelength range between 190 nanometers and 900 nanometers. These measurement channels may be configured as spectroscopic reflectometers, ellipsometers, scatterometers, or any combination thereof.

In some embodiments, a metrology system incorporates an infrared spectroscopic reflectometer as described herein and a spectroscopic ellipsometer operating in the wavelength range between 190 nanometers and 900 nanometers. The infrared spectroscopic reflectometer is configured to perform measurements at angles of incidence less than 40 degrees (e.g., between 5 degrees and 40 degrees) and the spectroscopic ellipsometer is configured to perform measurements at angles of incidence greater than 40 degrees (e.g., between 50 degrees and 90 degrees). In some of these embodiments, the measurement spot of the infrared spectroscopic reflectometer is co-located with the measurement spot of the spectroscopic ellipsometer. In some other embodiments, the measurement spots are not co-located.

In some embodiments, a metrology system incorporates one or more infrared spectroscopic reflectometer measurement channels as described herein that operate in the wavelength range between 750 nanometers and 2600 nanometers. In addition, the metrology system includes one or more additional channels including, but not limited to at least one UV to near IR spectrometer channel utilizing a UV to near IR detector, such as a CCD sensor measuring in the wavelength range from 190 nanometers to 900 nanometers, at least one vacuum UV spectrometer channel utilizing a vacuum UV CCD sensor measuring in the wavelength range from 150 nanometers to 300 nanometers, at least one mid IR spectrometer channel measuring in the wavelength range between 2500 nanometers to 4500 nanometers, or any combination thereof.

In some embodiments, one or more measurement channels of the metrology system are configured to measure the wafer at different azimuth angles, in addition to different ranges of wavelength and angle of incidence. In some embodiments, a metrology system including an infrared spectroscopic reflectometer as described herein is configured to perform measurements of the wafer at azimuth angles of zero and ninety degrees relative to the metrology target. In some embodiments, the metrology system is configured to measure wafer reflectivity over one or more wavelength ranges, one or more AOI ranges, and one or more azimuth angles simultaneously.

The foregoing is a summary and thus contains, by necessity, simplifications, generalizations and omissions of detail; consequently, those skilled in the art will appreciate that the summary is illustrative only and is not limiting in any way. Other aspects, inventive features, and advantages of the devices and/or processes described herein will become apparent in the non-limiting detailed description set forth herein.

BRIEF DESCRIPTION OF THE DRAWINGS

FIG. 3 depicts a chart 165 illustrating simulation results predicting expected 3-sigma measurement precision in various measurement scenarios.

FIG. 4 depicts an amorphous carbon layer 166 disposed on top of a silicon substrate 167 under measurement by an ellipsometer and a reflectometer.

FIG. 5 depicts the reflectivity of s-polarized illumination light versus the p-polarized illumination light as a function of angle of incidence.

DETAILED DESCRIPTION

Figure 1:
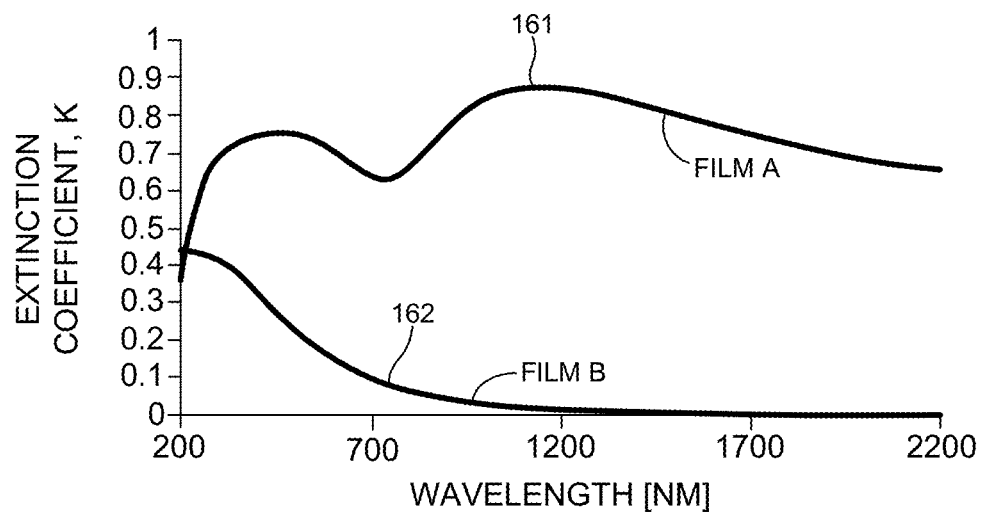
FIG. 1 depicts a plot of the extinction coefficient of two amorphous carbon films that are used as hardmask materials in etch steps of the semiconductor fabrication process.

Reference will now be made in detail to background examples and some embodiments of the invention, examples of which are illustrated in the accompanying drawings.

Methods and systems for performing spectroscopic reflectometry measurements of semiconductor structures at infrared wavelengths are presented herein. In some embodiments, spectra including ultraviolet, visible, and infrared wavelengths are simultaneously measured at high throughput with the same alignment conditions. In this manner, machine errors, such as wavelength errors, are uniformly corrected across all measured wavelengths. In a further aspect, the spectroscopic measurements are performed off-axis from the direction normal to the surface of the wafer to reduce the influence of backside reflections on the measurement results. In another further aspect, a broad range of wavelengths are detected by a detector that includes multiple photosensitive areas having different sensitivity characteristics. Collected light is linearly dispersed across the surface of the detector according to wavelength. Each different photosensitive area is arranged on the detector to sense a different range of incident wavelengths. In this manner, a broad range of wavelengths are detected with high signal to noise ratio by a single detector. These features, individually, or in combination, enable high throughput measurements of high aspect ratio structures (e.g., structures having depths of one micrometer or more) with high throughput, precision, and accuracy.

By simultaneously measuring a target with infrared, visible, and ultraviolet light in a single system, precise characterization of complex three dimensional structures is enabled. In general, relatively long wavelengths penetrate deep into a structure and provide suppression of high diffraction orders when measuring structures with relatively large pitch. Relatively short wavelengths provide precise dimensional information about structures accessible to relatively short wavelengths (i.e., top level layers) as well as relatively small CD and roughness features. In some examples, longer wavelengths enable measurement of dimensional characteristics of targets with relatively rough surfaces or interfaces due to lower sensitivity of longer wavelengths to roughness.

In some embodiments, the methods and systems for spectroscopic metrology of semiconductor devices described herein are applied to the measurement of high aspect ratio (HAR), large lateral dimension structures, or both. These embodiments enable optical critical dimension (CD), film, and composition metrology for semiconductor devices with HAR structures (e.g., NAND, VNAND, TCAT, DRAM, etc.) and, more generally, for complex devices that suffer from low light penetration into the structure(s) being measured. HAR structures often include hard mask layers to facilitate etch processes for HARs. As described herein, the term "HAR structure" refers to any structure characterized by an aspect ratio that exceeds 2:1 or 10:1, and may be as high as 100:1, or higher.

FIG. 1 depicts a plot of the extinction coefficient of two amorphous carbon films that are used as hardmask materials in etch steps of the fabrication process for three dimensional NAND structures. Plotline 161 depicts the extinction coefficient as a function of wavelength for an amorphous carbon film A, and plotline 162 depicts the extinction coefficient as a function of wavelength for an amorphous carbon film B. The extinction coefficient of film A maintains a relatively high value throughout the wavelength range from 200 nanometers to 2200 nanometers. Thus, film A is strongly absorbing even through the near IR spectral regions.

Figure 2:
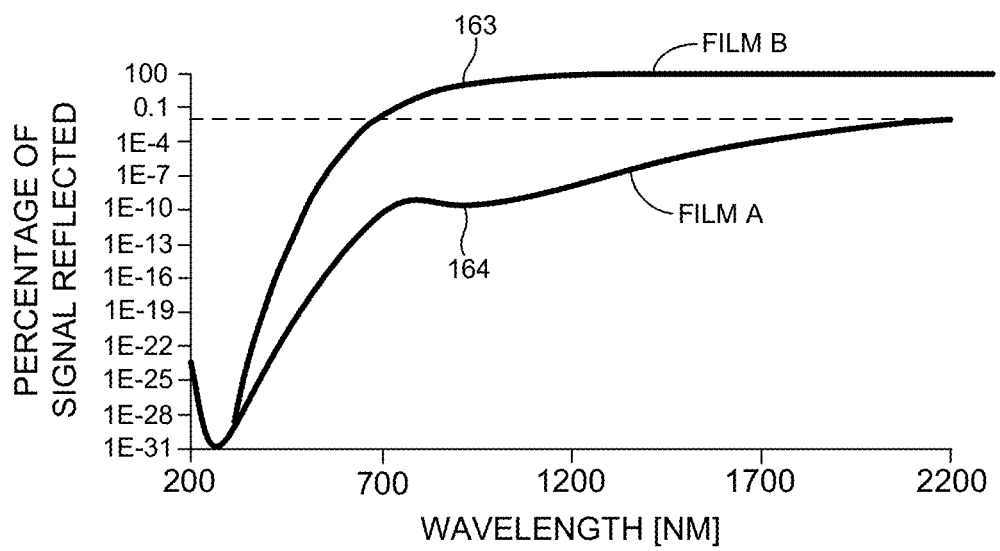
FIG. 2 depicts a plot of the percentage of light reflected from the two amorphous carbon films illustrated in FIG. 1.

FIG. 2 depicts a plot of the percentage of light reflected from films A and B having a thickness of 12,500 Angstroms as measured by a reflectometer. The percentage of light reflected from film A remains extremely low throughout the range of wavelengths from 200 nanometers to 2200 nanometers. As illustrated in FIG. 2, the minimum wavelength required to collect approximately 0.05% of incident light is approximately 2000 nanometers. Below approximately 1800 nanometers the amount of collected signal is practically immeasurable.

FIGS. 1 and 2 illustrate the importance of employing short wavelength infrared light (e.g., 1400 nanometer to 3000 nanometer), and even mid wavelength infrared light (e.g., 3000 nanometer through 5000 nanometer, and beyond) to perform reflectance based measurements of important materials employed in semiconductor manufacture.

In addition, reflectometer and ellipsometer configurations demonstrate different effectivity when measuring high extinction ratio materials. FIG. 3 depicts a chart 165 illustrating simulation results predicting the 3-sigma measurement precision expected in various measurement scenarios. Film thickness measurements of an amorphous carbon layer at two different thicknesses (15,000 Angstroms and 20,000 Angstroms) are simulated, both in a spectroscopic reflectometer configuration and a spectroscopic ellipsometer configuration. In addition, two different ranges of illumination wavelengths are considered. In one scenario SE and SR measurements are simulated with illumination wavelengths ranging from 950 nanometers to 2200 nanometers. In another scenario, SE and SR measurements are simulated with illumination wavelengths ranging from 950 nanometers to 2500 nanometers. As illustrated in FIG. 3, the SR configuration achieves significantly greater measurement precision compared to the SE measurements. In addition, measurements performed at the extended range of illumination wavelengths also achieve greater measurement precision.

Because the reflectometer operates at or near normal incidence, it has a "path length" advantage over an ellipsometer. FIG. 4 depicts an amorphous carbon layer 166 disposed on top of a silicon substrate 167. In an ellipsometer configuration, illumination light 168 is incident to film 166 at a relatively large angle (e.g., angle of incidence greater than 40 degrees). The light refracts at the air-film interface and propagates through film 166 at an angle of refraction that is significantly greater than zero. Similarly, light reflected from the bottom surface of film 166 propagates through film 166 at the angle of refraction, refracts at the air-film interface and propagates to a detector of the SE system. In contrast, in a reflectometer configuration, illumination light 170 is incident to film 166 at a relatively small angle (e.g., zero angle for the case of normal incidence reflectometry). At normal incidence, the light propagates through film 166 without refraction and reflects back directly from the bottom surface of film 166. The reflected light 171 propagates to the SR detector. As depicted in FIG. 4, the optical path length of the illumination light and the reflected light through film 166 is longer in an SE configuration than an SR configuration. This additional optical path length in film 166 leads to additional absorption and loss of measurement signal. For this reason, a relatively small angle SR configuration is preferable to a relatively large angle SE configuration for measurements of highly absorptive materials such as amorphous carbon layers.

Figure 6:
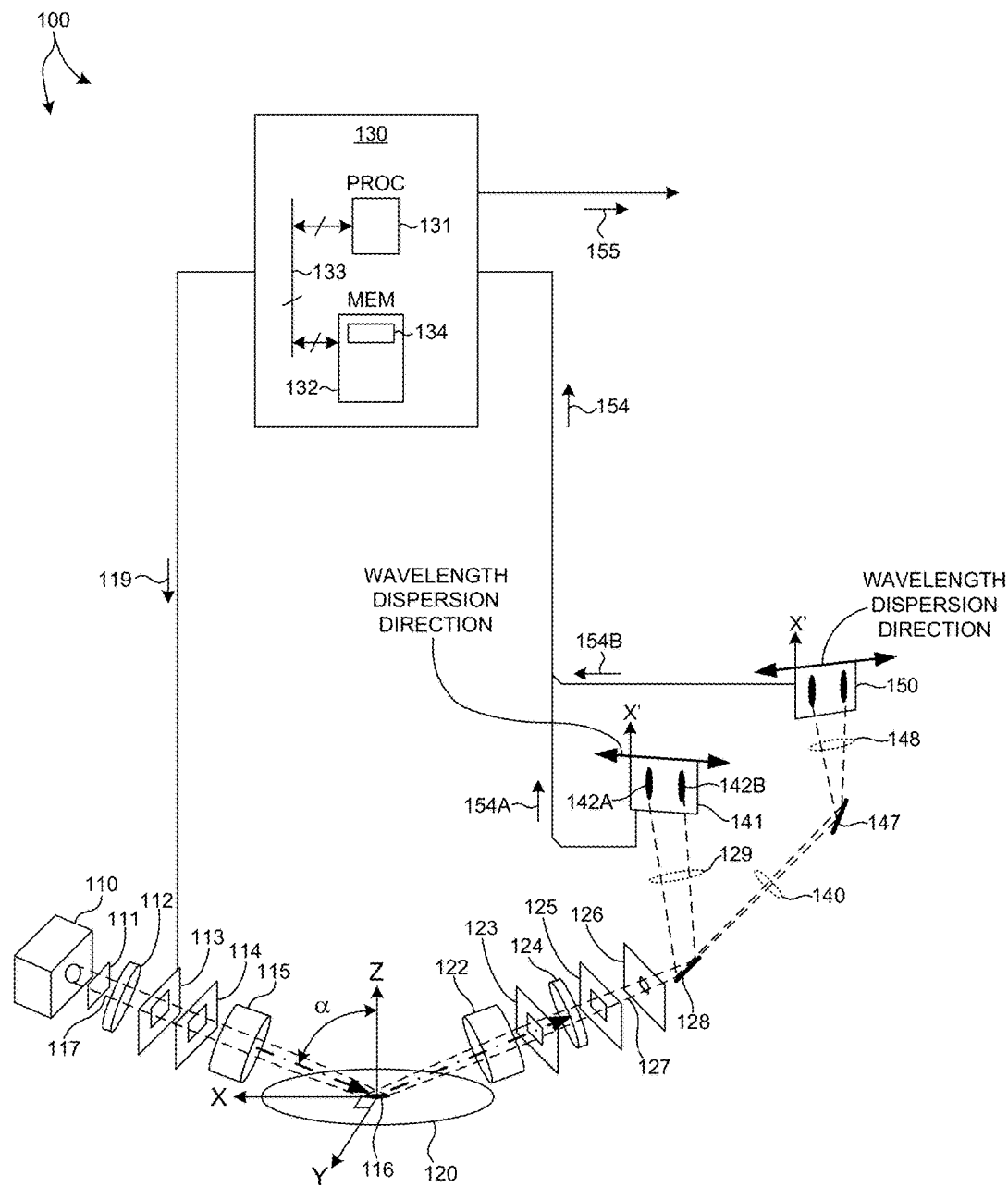
FIG. 6 depicts an exemplary metrology system 100 for performing broadband infrared spectroscopic reflectometry measurements of semiconductor structures.

FIG. 5 depicts the reflectivity of s-polarized illumination light versus the p-polarized illumination light as a function of angle of incidence. Plotline 172 depicts the reflectivity of s-polarized light and plotline 173 depicts the reflectivity of p-polarized light. As illustrated in FIG. 6, the reflectivity of p-polarized light declines significantly in the typical angular range employed in SE measurements (e.g., AOI greater than 40 degrees). The decline is particularly acute near the Brewster angle. As illustrated in FIG. 5, to avoid significant declines in reflectivity of p-polarized light, a small angle SR configuration (e.g., AOI less than 40 degrees) is preferable.

In one aspect, an infrared spectroscopic reflectometer including one or more measurement channels spanning a wavelength range between 750 nanometers and 2600 nanometers is employed to perform measurements of semiconductor structures. The one or more measurement channels are operable in parallel (i.e., simultaneous measurement of the sample throughout the wavelength range) or in sequence (i.e., sequential measurement of the sample throughout the wavelength range).

FIG. 6 depicts an exemplary, metrology system 100 for performing broadband infrared spectroscopic reflectometry measurements of semiconductor structures (e.g., film thickness, critical dimensions, overlay, etc.). In some examples, the one or more structures include at least one high aspect ratio (HAR) structure or at least one large lateral dimension structure. As depicted in FIG. 6, metrology system 100 is configured as an oblique incidence, broadband spectroscopic reflectometer. However, in general, metrology system 100 may also include additional spectroscopic reflectometers, a spectroscopic ellipsometer, scatterometer, or any combination thereof.

Metrology system 100 includes an illumination source 110 that generates a beam of illumination light 117 incident on a wafer 120. In some embodiments, illumination source 110 is a broadband illumination source that emits illumination light in the ultraviolet, visible, and infrared spectra. In one embodiment, illumination source 110 is a laser sustained plasma (LSP) light source (a.k.a., laser driven plasma source). The pump laser of the LSP light source may be continuous wave or pulsed. A laser-driven plasma source can produce significantly more photons than a Xenon lamp across the entire wavelength range from 150 nanometers to 2000 nanometers. Illumination source 110 can be a single light source or a combination of a plurality of broadband or discrete wavelength light sources. The light generated by illumination source 110 includes a continuous spectrum or parts of a continuous spectrum, from ultraviolet to infrared (e.g., vacuum ultraviolet to mid infrared). In general, illumination light source 110 may include a super continuum laser source, an infrared helium-neon laser source, an arc lamp (e.g., a Xenon arc lamp), a deuterium lamp, or any other suitable light source.

In a further aspect, the amount of illumination light is broadband illumination light that includes a range of wavelengths spanning at least 500 nanometers. In one example, the broadband illumination light includes wavelengths below 250 nanometers and wavelengths above 750 nanometers. In general, the broadband illumination light includes wavelengths between 120 nanometers and 3,000 nanometers. In some embodiments, broadband illumination light including wavelengths beyond 3,000 nanometers may be employed. In some examples, broadband illumination light includes wavelengths up to 5,000 nanometers.

As depicted in FIG. 6, metrology system 100 includes an illumination subsystem configured to direct illumination light 117 to one or more structures formed on the wafer 120. The illumination subsystem is shown to include light source 110, one or more optical filters 111, polarizing component 112, field stop 113, aperture stop 114, and illumination optics 115. The one or more optical filters 111 are used to control light level, spectral output, or both, from the illumination subsystem. In some examples, one or more multi-zone filters are employed as optical filters 111. Polarizing component 112 generates the desired polarization state exiting the illumination subsystem. In some embodiments, the polarizing component is a polarizer, a compensator, or both, and may include any suitable commercially available polarizing component. The polarizing component can be fixed or rotatable to different fixed positions. Although the illumination subsystem depicted in FIG. 6 includes one polarizing component, the illumination subsystem may include more than one polarizing component. Field stop 113 controls the field of view (FOV) of the illumination subsystem and may include any suitable commercially available field stop. Aperture stop 114 controls the numerical aperture (NA) of the illumination subsystem and may include any suitable commercially available aperture stop. Light from illumination source 110 is directed through illumination optics 115 to be focused on one or more structures (not shown in FIG. 6) on wafer 120. The illumination subsystem may include any type and arrangement of optical filter(s) 111, polarizing component 112, field stop 113, aperture stop 114, and illumination optics 115 known in the art of spectroscopic reflectometry.

As depicted, in FIG. 6, the beam of illumination light 117 passes through optical filter(s) 111, polarizing component 112, field stop 113, aperture stop 114, and illumination optics 115 as the beam propagates from the illumination source 110 to wafer 120. Beam 117 illuminates a portion of wafer 120 over a measurement spot 116.

In some examples, the beam size of the amount of illumination light 117 projected onto the surface of wafer 120 is smaller than a size of a measurement target that is measured on the surface of the specimen. Exemplary beam shaping techniques are described in detail in U.S. Patent Application Publication No. 2013/0114085 by Wang et al., the contents of which are incorporated herein by reference in their entirety.

Metrology system 100 also includes a collection optics subsystem configured to collect light generated by the interaction between the one or more structures and the incident illumination beam 117. A beam of collected light 127 is collected from measurement spot 116 by collection optics 122. Collected light 127 passes through collection aperture stop 123, polarizing element 124 and field stop 125 of the collection optics subsystem.

Collection optics 122 includes any suitable optical elements to collect light from the one or more structures formed on wafer 120. Collection aperture stop 123 controls the NA of the collection optics subsystem. Polarizing element 124 analyzes the desired polarization state. The polarizing element 124 is an analyzer or a compensator. The polarizing element 124 can be fixed or rotatable to different fixed positions. Although the collection subsystem depicted in FIG. 6 includes one polarizing element, the collection subsystem may include more than one polarizing element. Collection field stop 125 controls the FOV of the collection subsystem. The collection subsystem takes light from wafer 120 and directs the light through collection optics 122 and polarizing element 124 to be focused on collection field stop 125. In some embodiments, collection field stop 125 is used as a spectrometer slit for the spectrometers of the detection subsystem. However, collection field stop 125 may be located at or near a spectrometer slit 126 of the spectrometers of the detection subsystem.

The collection subsystem may include any type and arrangement of collection optics 122, aperture stop 123, polarizing element 124, and field stop 125 known in the art of spectroscopic reflectometry.

In the embodiment depicted in FIG. 6, the collection optics subsystem directs light to more than one spectrometer of the detection subsystem. The detection subsystem generates output responsive to light collected from the one or more structures illuminated by the illumination subsystem.

In one aspect, the detector subsystem includes two or more detectors each configured to detect collected light over different wavelength ranges, including infrared, simultaneously.

In the embodiment depicted in FIG. 6, collected light 127 passes through spectrometer slit 126 and is incident on diffractive element 128. Diffractive element 128 is configured to diffract a subset of wavelengths of the incident light into the +/−1 diffraction order and diffract a different subset of wavelengths of the incident light into the zero diffraction order. As depicted in FIG. 6, portion 129 of the incident light including the ultraviolet spectrum is dispersed at the +/−1 diffraction order toward detector 141 by diffractive element 128. In addition, diffractive element 128 is configured to reflect portion 140 of the incident light including infrared wavelengths at the zero diffraction order toward grating 147. Light 140 is incident on diffractive element 147 and diffractive element 147 disperses portion 148 of the incident light 140 including infrared wavelengths at the +/−1 diffraction order toward detector 150.

In the embodiment depicted in FIG. 6, diffractive element 128 is a reflective grating element. However, in general, diffractive element 128 may be configured to subdivide the incident light into different wavelength bands, propagate the different wavelength bands in different directions, and disperse the light of one of the wavelength bands onto a detector in any suitable manner. In one example, diffractive element 128 is configured as a transmissive grating. In some other examples, diffractive element 128 includes a beam-splitting element to subdivide the beam into different wavelength bands and a reflective or transmissive grating structure to disperse one of the wavelength bands onto detector 141.

Reflective grating 128 is employed because it exhibits high diffraction efficiency into the +/−1 orders in the ultraviolet spectral region and high diffraction efficiency into the zeroth diffraction order for the infrared spectral region. By employing a reflective grating, losses inherent to beam splitting elements (such as a dichroic beam splitting element) are avoided.

The diffractive elements 128 and 147 linearly disperse first order diffracted light according to wavelength along one dimension of each respective two dimensional detector (i.e., the wavelength dispersion direction noted in FIG. 6 for each respective detector). For purposes of illustration, light detected at two different wavelengths is illustrated on the surface of detector 141. Diffractive element 128 causes a spatial separation between the two different wavelengths of light projected onto the surface of detector 141. In this manner, light collected from measurement spot 116 having a particular wavelength is projected onto detector 141 over spot 142A and light collected from measurement spot 116 having another, different wavelength is projected onto detector 141 over spot 142B.

In one example, detector 141 is a charge coupled device (CCD) sensitive to ultraviolet and visible light (e.g., light having wavelengths between 190 nanometers and 860 nanometers). In one example, detector 150 is a photo detector array (PDA) sensitive to infrared light (e.g., light having wavelengths between 950 nanometers and 5000 nanometers). However, in general, other two dimensional detector technologies may be contemplated (e.g., a position sensitive detector (PSD), an infrared detector, a photovoltaic detector, etc.). Each detector converts the incident light into electrical signals indicative of the spectral intensity of the incident light. For example, UV detector 141 generates output signals 154A indicative of incident light 129 and IR detector 150 generates output signals 154B indicative of incident light 148.

As depicted in FIG. 6, the detection subsystem is arranged such that the collected light propagates to all detectors of metrology system 100, simultaneously. Metrology system 100 also includes computing system 130 configured to receive detected signals 154, including both UV and IR signals, and determines an estimate 155 of a value of a parameter of interest of the measured structure(s) based on both the UV and IR signals. By simultaneously collecting UV and IR spectra measurement times are reduced and all spectra are measured with the same alignment conditions. This allows wavelength errors to be corrected more easily because a common correction can be applied to all spectral data sets.

In another aspect, one or more of the infrared spectroscopic reflectometers described herein employ off-axis illumination, collection, or both, to reject measurement signals generated by reflections from the bottom of the underlying substrate.

Figure 7:
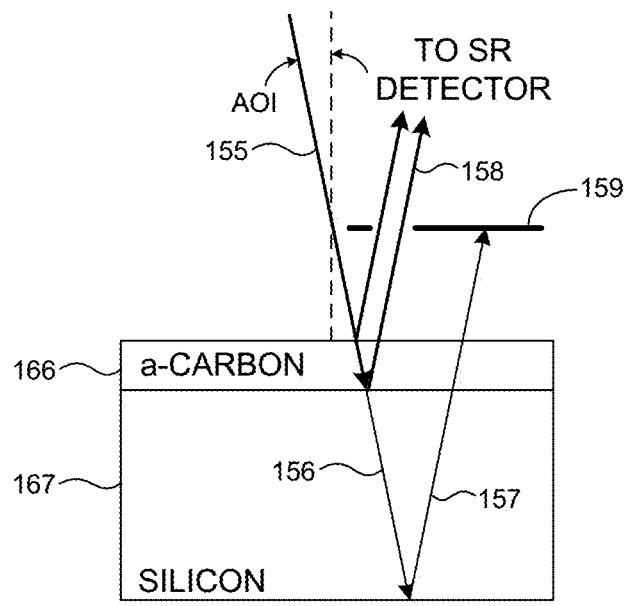
FIG. 7 depicts illumination incident onto a film layer disposed on a substrate at near normal incidence, but specifically avoiding normal incidence.

FIG. 7 depicts illumination 155 incident onto film layer 166, which is disposed on substrate 167. As depicted in FIG. 5, the illumination is arranged at near normal incidence, but specifically avoiding normal incidence (AOI=zero degrees). A portion of incident light reflects from the surface of film 166, another portion 158 reflects from the interface between film 166 and substrate 167. These reflections are desirable and must be collected to estimate the thickness of film 166 based on a reflectometry technique. However, in addition, a portion 156 of the incident light 155 penetrates the substrate 167. A portion 157 of light 156 reflects from the bottom of the substrate (e.g., the backside of a wafer), propagates through substrate 167 and film 166. Light 157 is undesirable and contaminates the measurement of film 166. As depicted in FIG. 7, a collection aperture 159 is successfully employed to block the undesirable light 157 reflected from the back surface of the substrate 167. This is possible because the non-zero angle of incidence of the illumination creates a spatial separation between light reflected from the top and bottom surfaces of film 166 and light 157 reflected from the bottom of substrate 167.

Figure 8:
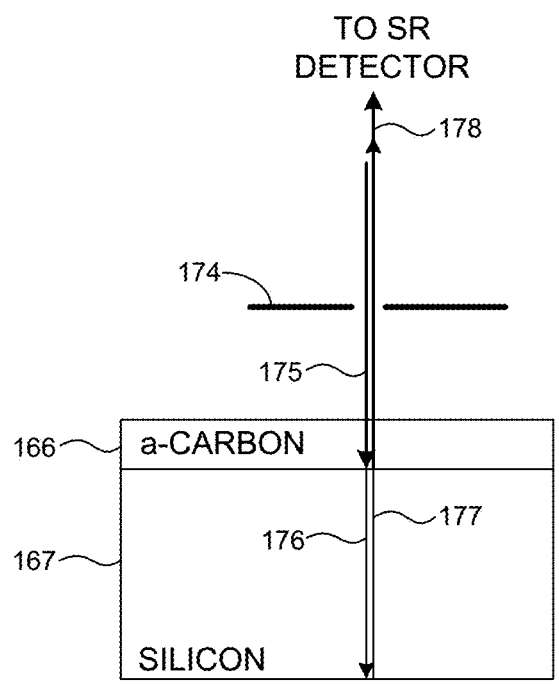
FIG. 8 depicts illumination incident onto a film layer disposed on a substrate at normal incidence.

In contrast, FIG. 8 depicts illumination 175 incident onto film layer 166, which is disposed on substrate 167. As depicted in FIG. 8, the illumination is arranged at normal incidence. A portion of incident light 175 reflects from the surface of film 166, another portion reflects from the interface between film 166 and substrate 167. In addition, a portion 176 of the incident light 175 penetrates the substrate 167. A portion 177 of light 176 reflects from the bottom of the substrate (e.g., the backside of a wafer), propagates through substrate 167 and film 166. Light 177 is undesirable and contaminates the measurement of film 166. As depicted in FIG. 8, a collection aperture 174 is unable to block the undesirable light 177 reflected from the back surface of the substrate 167 because the zero angle of incidence of the illumination does not generate spatial separation between light reflected from the top and bottom surfaces of film 166 and light 177 reflected from the bottom of substrate 167.

Thus, in some embodiments, it is preferable to perform infrared reflectrometry measurements as described herein at non-zero angles of incidence. In this manner, light generated from backside reflections can be effectively blocked from the measurement. In some embodiments, oblique illumination is employed to reduce measurement sensitivity to backside reflections as described with reference to FIG. 7, and also illustrated in embodiments of FIG. 9. In some other embodiments, normal illumination is employed, but an obscuration mask 223 in the collection path at or near the collection aperture stop or its conjugates, is employed to block the central rays over the numerical aperture such that the back side reflection is not admitted into the measurement optics as illustrated in embodiment of FIG. 10. This approach enables normal illumination incidence, but suffers from possible disadvantages such as a centrally obscured pupil, light loss, and algorithmic complexity. In some other embodiments, obscuration 223 is located in the illumination path.

Figure 9:
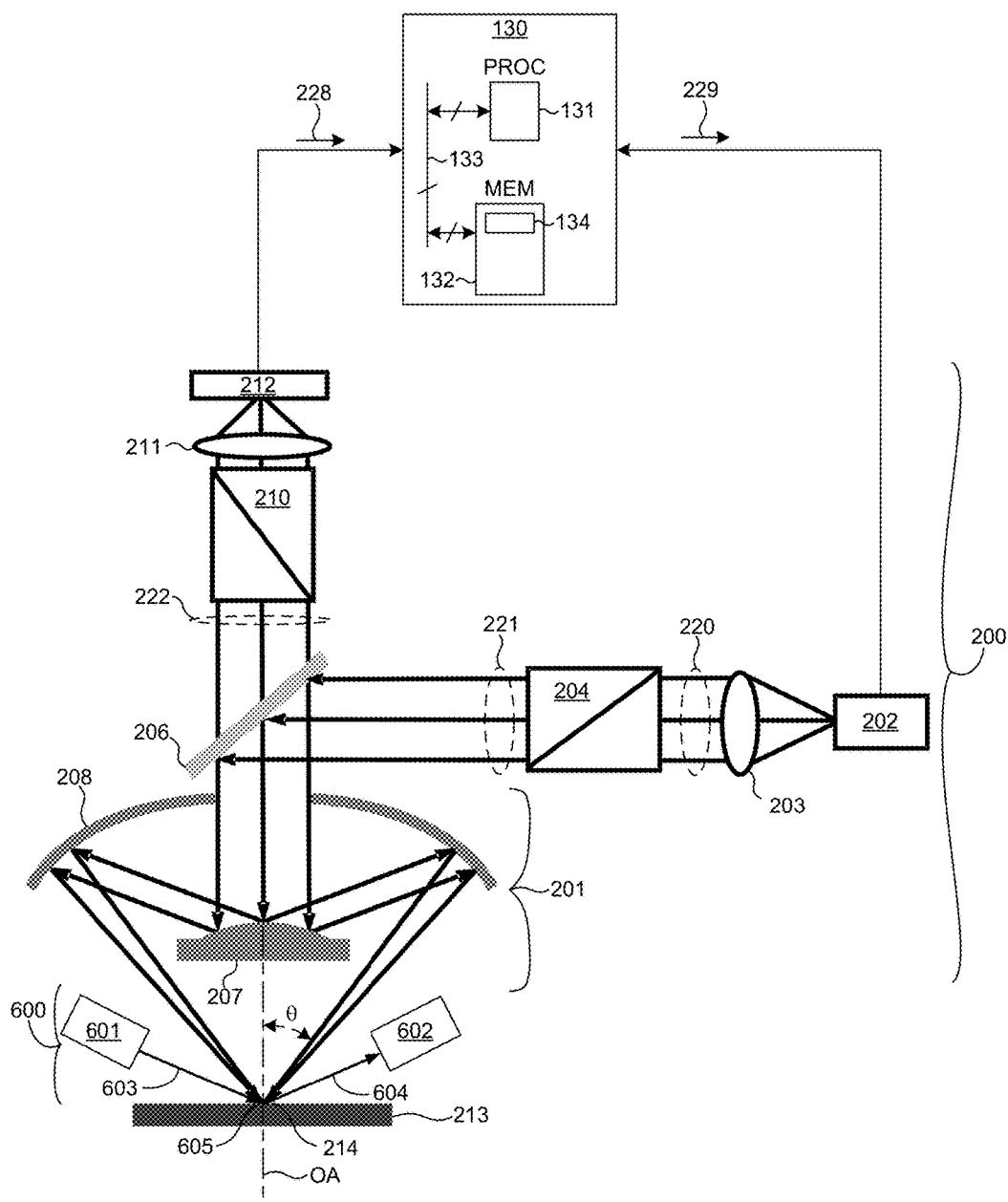
FIG. 9 depicts an exemplary metrology system 200 for performing broadband infrared spectroscopic reflectometry measurements of semiconductor structures.

FIG. 9 depicts an infrared spectroscopic reflectometer including one or more measurement channels spanning a wavelength range between 750 nanometers and 2600 nanometers in another embodiment. In one aspect, infrared spectroscopic reflectometer 200 includes a Schwartzchild objective to avoid normal incidence. Like numbered elements illustrated in FIG. 9 are analogous to those described with reference to FIG. 6.

Infrared spectroscopic reflectometer 200 includes polarizer 204, objective 201, analyzer 210, and spectrometer 212. As depicted in FIG. 9, a light beam is generated by the illumination source 202 in response to command signals received from computing system 130. Light from illumination source 202 is conditioned by optional beam forming optics 203 to generate an illumination light beam 220. Illumination light beam 220 is directed to polarizer 204.

Although, as depicted, illumination light directed to polarizer 204 comes from illumination source 202, in general, light from any of the illumination sources of system 100 may be combined to generate an illumination light beam directed to polarizer 204. In this manner, the spectral components of the illumination light can be configured as a combination of light emitted from multiple illumination sources.

In some embodiments, polarizer 204 is configured to selectively rotate a polarizing element about the optical axis of the illumination light beam 220. In general, polarizer 204 may include any polarizing element and system to rotate the polarizing element known in the art. For example, the polarizer 204 may include a polarizing element mechanically coupled to a rotational actuator. In one example, the polarizing element may be a Rochon prism. In another example, the polarizing element may include a beam displacer. Polarizer 204 is configured to operate within system 200 in either a rotationally active or rotationally inactive state. In one instance, a rotational actuator of polarizer 204 may be inactive such that the polarizing element remains rotationally fixed about the optical axis of illumination light 220. In another instance, the rotational actuator may rotate the polarizing element at a selected angular frequency, $\omega_p$, about the optical axis of the illumination light.

In some other embodiments, polarizer 204 is configured with a fixed polarization angle about the optical axis of the illumination light beam 220.

As depicted in FIG. 9, illumination light beam 220 passes through polarizer 204 while the rotational actuator rotates the polarizing element at the selected angular frequency, $\omega_p$. In this manner, polarizer 204 generates a polarized light beam 221 directed toward beamsplitter 206. Beamsplitter 206 directs the polarized light beam 221 towards objective 201.

In the embodiment depicted in FIG. 9, objective 201 is a Schwartzschild type objective including reflective optical elements only. The Schwartzschild objective depicted in FIG. 9 includes a concave mirror 208 with an opening (e.g., hole) aligned with the optical axis, OA, to allow light to pass in and out of the objective 201. Incoming light passes through the opening, and reflects off convex mirror 207 toward concave mirror 208. The reflected light is focused on the surface of wafer 213 by concave mirror 208. The polarized light beam 221 is focused onto the surface of wafer 213 over a range of angles of incidence by objective 201, but not at a zero angle of incidence (i.e., normal to the surface of wafer 213). In some examples, polarized light beam 221 is focused onto the surface of wafer 213 within a range of angles of incidence between 5 and 40 degrees. In some other examples, polarized light beam 221 is focused onto the surface of wafer 213 within a range of angles of incidence between 5 and 25 degrees. In some examples, a portion of polarized light beam 221 is focused onto the surface of wafer 213 at an angle of incidence less than 20 degrees. In some other examples, a portion of polarized light beam 221 is focused onto the surface of wafer 213 at an angle of incidence less than 15 degrees. In some examples, the polarized light beam 221 is focused onto the surface of wafer 213 at small angles of incidence results in a small illumination spot. In some examples, the resulting illumination spot is less than 20 micrometers in diameter. In some other examples, the resulting illumination spot size is less than 10 micrometers in diameter.

The interaction of the focused, polarized light beam 221 with wafer 213 modifies the polarization of the radiation by any of reflection, scattering, diffraction, transmission, or other types of processes. After interaction with the wafer 213, modified light 222 is collected by objective 201 over a measurement spot 214 and directed to beamsplitter 206. Light from wafer 213 is collected by concave mirror 208 and focused onto convex mirror 207 where it exits the Schwartzschild objective through the same hole as the incoming light toward beamsplitter 206. Beamsplitter 206 is configured to transmit modified light 222 toward analyzer 210. In the embodiment depicted in FIG. 9, analyzer 210 includes a polarizer element that remains rotationally fixed about the optical axis of modified light beam 222 while the modified light beam 222 passes through the analyzer 210 and optional beam focusing optics 211 to spectrometer 212. In spectrometer 212, the beam components having different wavelengths are refracted (e.g., in a prism spectrometer) or diffracted (e.g., in a grating spectrometer) in different directions to different detectors. The detectors may be a linear array of photodiodes, with each photodiode measuring radiation in a different wavelength range. The radiation received by the spectrometer 212 is analyzed with regard to polarization state, allowing for spectral analysis by the spectrometer of radiation passed by the polarizer 204. These spectra 228 are passed to computing system 130 for analysis of the structural characteristics of wafer 213.

Figure 10:
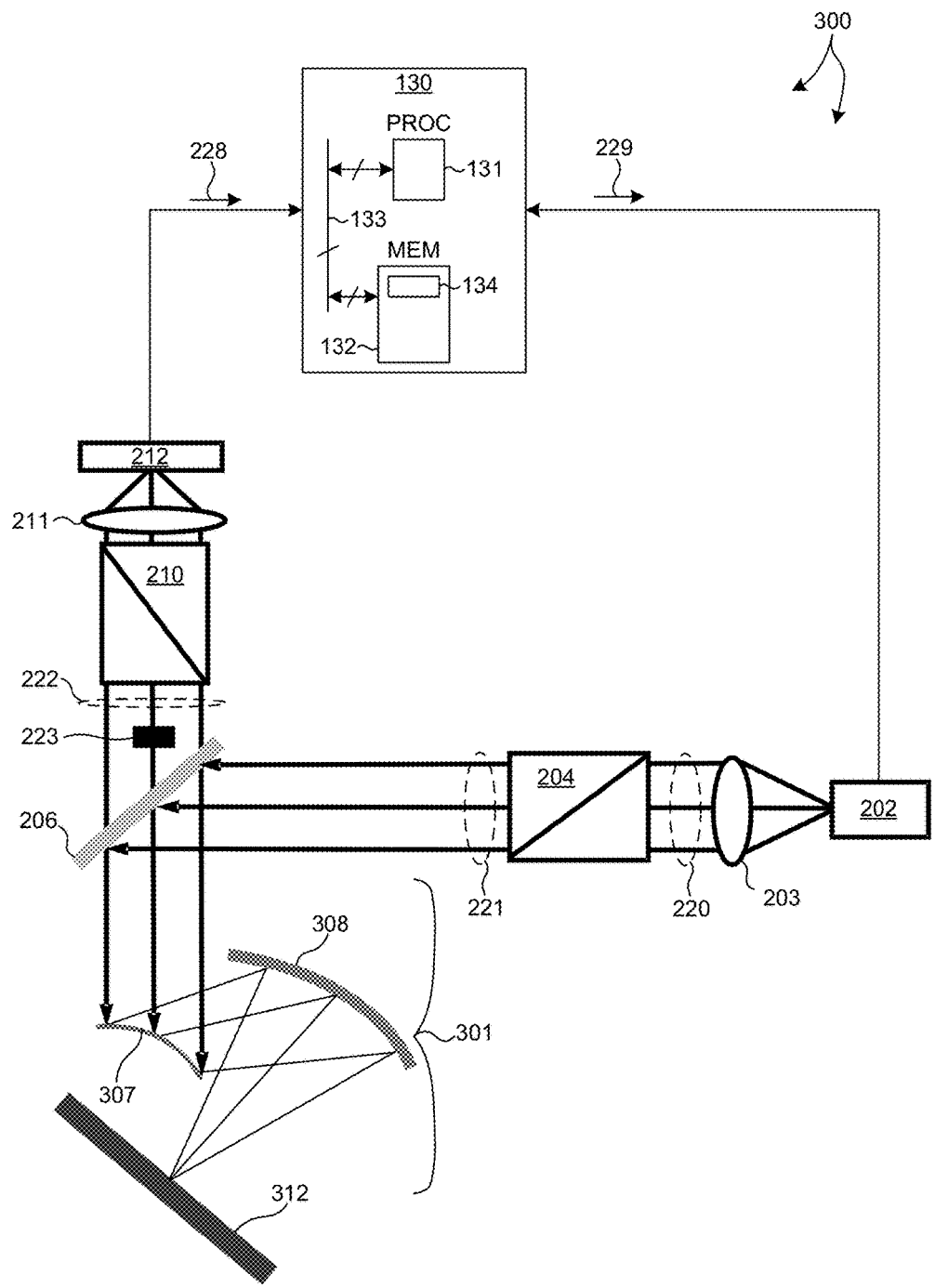
FIG. 10 depicts an exemplary metrology system 300 for performing broadband infrared spectroscopic reflectometry measurements of semiconductor structures.

FIG. 10 depicts an infrared spectroscopic reflectometer including one or more measurement channels spanning a wavelength range between 750 nanometers and 2600 nanometers in another embodiment. In one aspect, infrared spectroscopic reflectometer 300 includes an off-axis unobscured objective lens 301 to achieve oblique incidence. Like numbered elements illustrated in FIG. 10 are analogous to those described with reference to FIGS. 6 and 9.

Infrared spectroscopic reflectometer 300 is analogous to infrared spectroscopic reflectometer 200 described with reference to FIG. 9. However, instead of a Schwartzchild objective, an off-axis unobscured objective lens 301 is employed. Incoming light reflects off convex mirror 307 toward concave mirror 308. The reflected light is focused on the surface of wafer 312 by concave mirror 308. The polarized light beam 221 is focused onto the surface of wafer 312 over a range of angles of incidence by objective 301. In some examples, polarized light beam 221 is focused onto the surface of wafer 312 within a range of angles of incidence between 5 and 40 degrees. In some other examples, polarized light beam 221 is focused onto the surface of wafer 213 within a range of angles of incidence between 5 and 25 degrees. In some examples, a portion of polarized light beam 221 is focused onto the surface of wafer 312 at an angle of incidence less than 20 degrees. In some other examples, a portion of polarized light beam 221 is focused onto the surface of wafer 312 at an angle of incidence less than 15 degrees. Polarized light beam 221 is focused onto the surface of wafer 312 at small angles of incidence results in a small illumination spot. In some examples, the resulting illumination spot is less than 20 micrometers in diameter. In some other examples, the resulting illumination spot size is less than 10 micrometers in diameter. In some examples, an illumination mask with a central obscuration, such as mask 223 depicted in FIG. 6, is located at or near an illumination pupil.

The interaction of the focused, polarized light beam 221 with wafer 312 modifies the polarization of the radiation by any of reflection, scattering, diffraction, transmission, or other types of processes. After interaction with the wafer 312, modified light 222 is collected by objective 301 and directed to beamsplitter 206. Light from wafer 312 is collected by concave mirror 308 and focused onto convex mirror 307 where it is collimated and exits objective 301 toward beamsplitter 206. In some other examples, a collection mask having a central obscuration, such as mask 223 depicted in FIG. 10, is located at or near the collection pupil.

Exemplary implementations of off-axis unobscured objective lenses are described in detail in U.S. Patent Application Publication No. 2016/0139032 by Rampoldi et al., the contents of which are incorporated herein by reference in their entirety.

In some embodiments, a detector subsystem includes a multi-zone infrared detector that combines different sensitivity bands at different locations on a single detector package. The detector is configured to deliver a continuous spectrum of data at different sensitivities, depending on location of incidence.

Figure 12:
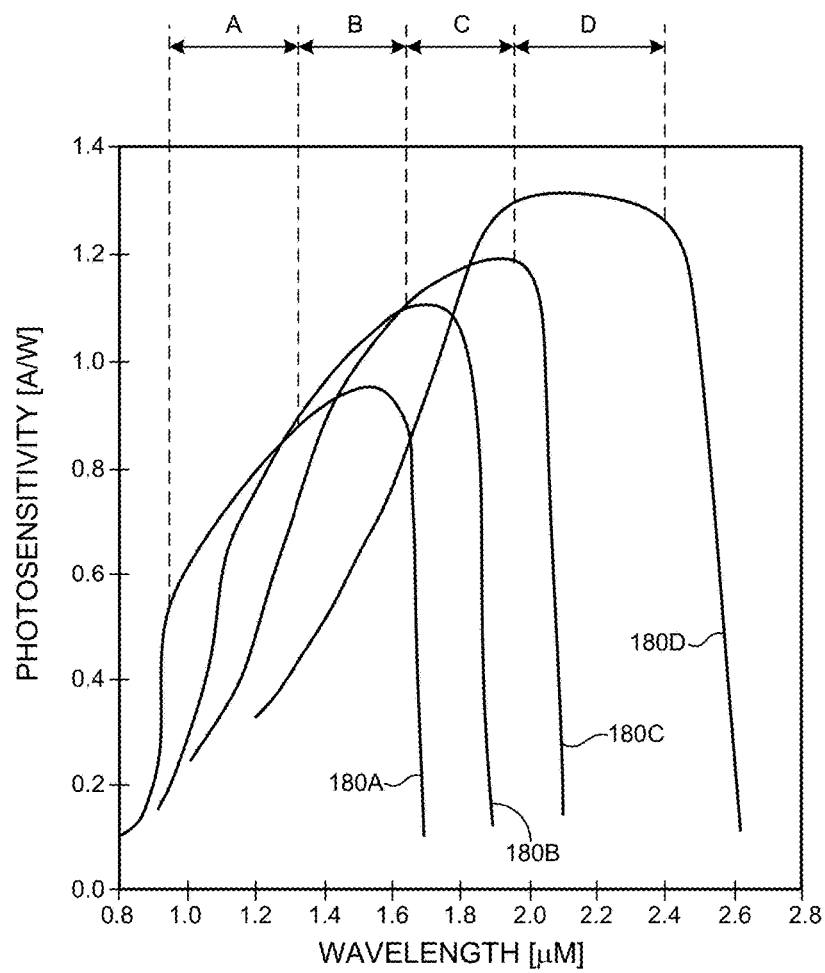
FIG. 12 illustrates typical photosensitivity curves of four available Indium Gallium Arsenide (InGaAs) sensors.

FIG. 12 illustrates typical photosensitivity curves of available Indium Gallium Arsenide (InGaAs) sensors. As depicted in FIG. 12, no single sensor of the available InGaAs sensors is capable of providing adequate photosensitivity across a wavelength band from 1 micrometer to 2.5 micrometers. Thus, individually, the available sensors are only capable of sensing over a narrow waveband.

In one aspect, multiple sensor chips, each sensitive in a different waveband are combined into a single detector package. In turn, this multi-zone detector is implemented in the metrology systems described herein.

Figure 11:
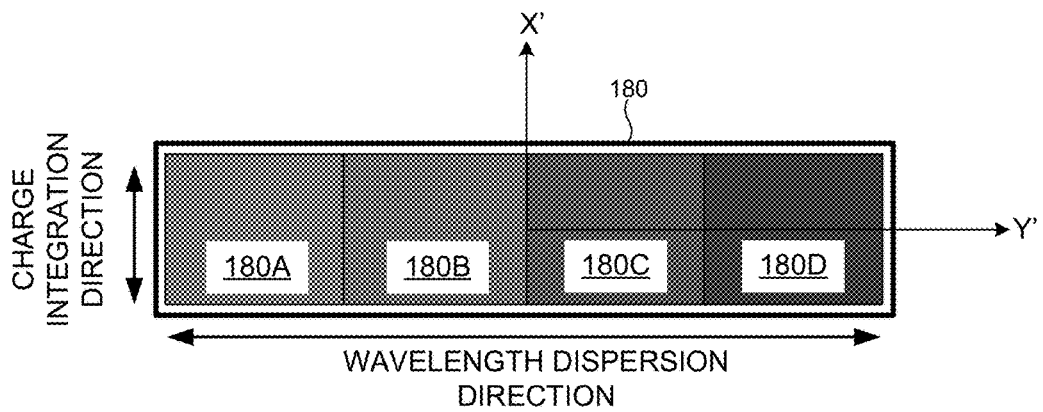
FIG. 11 depicts an illustration of a multi-zone infrared detector 180.

FIG. 11 depicts four sensor chips 180A-D derived from four different wavebands to make a multi-zone infrared detector 180. The four sensor chips include different material compositions that each exhibit different photosensitivity characteristics. As depicted in FIG. 11, sensor chip 180A exhibits high sensitivity over a waveband, A, sensor chip 180B exhibits high sensitivity over a waveband, B, sensor chip 180C exhibits high sensitivity over a waveband, C, and sensor chip 180D exhibits high sensitivity over a waveband, D. A metrology system incorporating detector 180 is configured to disperse wavelengths within waveband A onto sensor chip 180A, disperse wavelengths within waveband B onto sensor chip 180B, disperse wavelengths within waveband C onto sensor chip 180C, and disperse wavelengths within waveband D onto sensor chip 180D. In this manner, high photosensitivity (i.e., high SNR) is achieved over the aggregate waveband that includes wavebands A-D from a single detector. As a result measurement noise over the entire measurement range is reduced by limiting the use of a particular sensor to a narrowband where measurement sensitivity is high and measurement noise is low.

In some examples, a multi-zone detector includes InGaAs sensors with sensitivity to different spectral regions assembled in a single sensor package to produce a single, contiguous spectrum covering wavelengths from 750 nanometers to 3,000 nanometers, or beyond.

In general, any number of individual sensors may be assembled along the direction of wavelength dispersion of the multi-zone detector such that a contiguous spectrum maybe derived from the detector. However, typically, two to four individual sensors are employed in a multi-zone detector, such as detector 180.

In one embodiment, three individual sensors are employed with the first segment spanning the range between 800 nanometers and 1600 nanometers, the second segment spanning the range between 1600 nanometers and 2200 nanometers, and the third segment spanning the range between 2200 nanometers and 2600 nanometers.

Although, the use of InGaAs based infrared detectors is specifically described herein, in general, any suitable material that exhibits narrow sensitivity ranges and sharp sensitivity cutoffs may be integrated into a multi-zone detector as described herein.

As depicted in FIGS. 6, 9, and 10, the illustrated measurement channel includes a polarizer on the illumination side and an analyzer on the collection side. However, in general, it is contemplated that any measurement channel may include, or not include, an illumination polarizer, a collection analyzer, an illumination compensator, a collection compensator, in any combination, to perform measurements of the polarized reflectivity of the sample, unpolarized reflectivity of the sample, or both.

In a further aspect, a metrology system incorporating an infrared spectroscopic reflectometer as described herein may also include one or more additional measurement channels operating in the wavelength range between 190 nanometers and 900 nanometers. These measurement channels may be configured as spectroscopic reflectometers, ellipsometers, scatterometers, or any combination thereof.

In some embodiments, a metrology system incorporates an infrared spectroscopic reflectometer as described herein and a spectroscopic ellipsometer operating in the wavelength range between 190 nanometers and 900 nanometers. The infrared spectroscopic reflectometer is configured to perform measurements at angles of incidence less than 40 degrees (e.g., between 5 degrees and 40 degrees) and the spectroscopic ellipsometer is configured to perform measurements at angles of incidence greater than 40 degrees (e.g., between 50 degrees and 90 degrees). In some of these embodiments, the measurement spot of the infrared spectroscopic reflectometer is co-located with the measurement spot of the spectroscopic ellipsometer. In some other embodiments, the measurement spots are not co-located. For example, the metrology system depicted in FIG. 9 also includes a spectroscopic ellipsometer 600 including an illuminator 601 and a spectrometer 602. Illuminator 601 provides illumination radiation 603 to specimen 213. In response to the illumination, spectrometer 602 collects radiation 604 from specimen 213 over a measurement spot 605 that is co-located with the measurement spot 214 associated with infrared spectroscopic reflectometer 200.

In some embodiments, a metrology system incorporates one or more infrared spectroscopic reflectometer measurement channels as described herein that operate in the wavelength range between 750 nanometers and 2600 nanometers. In addition, the metrology system includes one or more additional channels including, but not limited to at least on UV to near IR spectrometer channel utilizing a UV to near IR detector, such as a CCD sensor measuring in the wavelength range from 190 nanometers to 900 nanometers, at least one vacuum UV spectrometer channel utilizing a vacuum UV CCD sensor measuring in the wavelength range from 150 nanometers to 300 nanometers, at least one mid IR spectrometer channel measuring in the wavelength range between 2500 nanometers to 4500 nanometers, or any combination thereof. In some of these embodiments, the measurement spots of the various spectrometers are co-located. In some other embodiments, the measurement spots are not co-located.

In some embodiments, one or more measurement channels of the metrology system are configured to measure the wafer at different azimuth angles, in addition to different ranges of wavelength and angle of incidence. In some embodiments, a metrology system including an infrared spectroscopic reflectometer as described herein is configured to perform measurements of the wafer at azimuth angles of zero and ninety degrees relative to the metrology target. In some embodiments, the metrology system is configured to measure wafer reflectivity over one or more wavelength ranges, one or more AOI ranges, and one or more azimuth angles simultaneously.

Figure 13A:
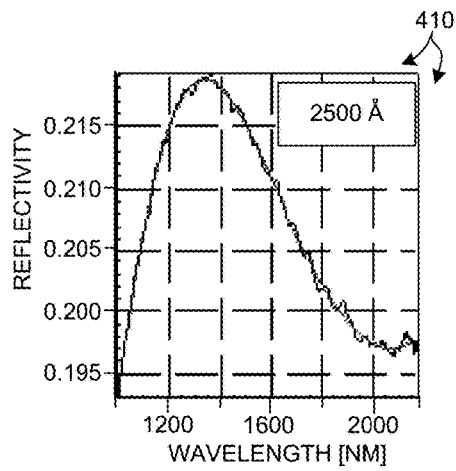
FIGS. 13A-E depicts experimental spectral measurements of reflectivity collected on amorphous carbon films using an infrared spectroscopic reflectometer as described herein.
Figure 13B:
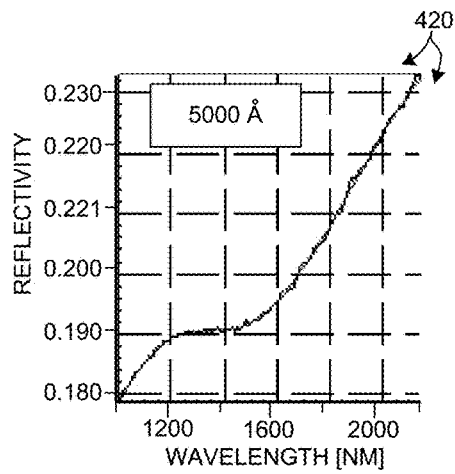
Figure 13C:
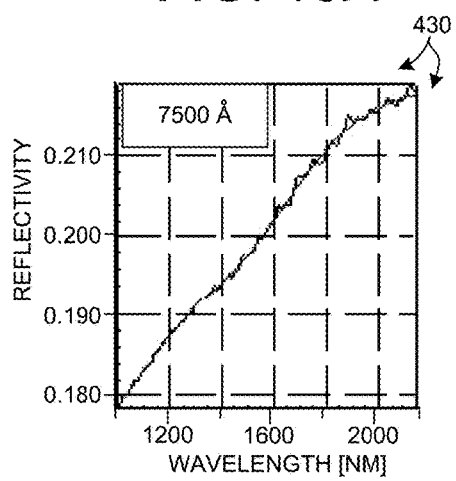
Figure 13D:
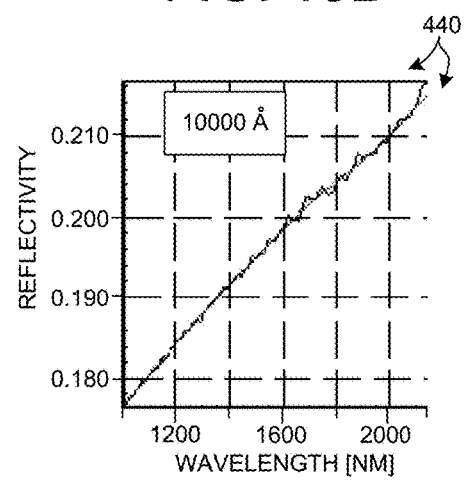
Figure 13E:
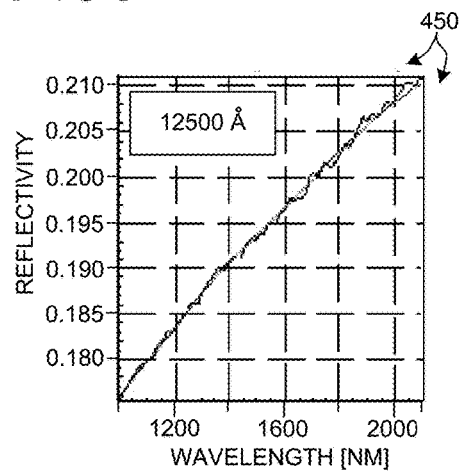

FIGS. 13A-E depict experimental spectral measurements of reflectivity collected on amorphous carbon films using an infrared spectroscopic reflectometer as described herein. FIG. 13A depicts a plot 410 of measurements of a film having a thickness of 2500 Angstroms. FIG. 13B depicts a plot 420 of measurements of a film having a thickness of 5000 Angstroms. FIG. 13C depicts a plot 430 of measurements of a film having a thickness of 7500 Angstroms. FIG. 13D depicts a plot 440 of measurements of a film having a thickness of 10000 Angstroms. FIG. 13E depicts a plot 450 of measurements of a film having a thickness of 12500 Angstroms. As depicted in FIGS. 13A-E, as film thickness increase, absorption losses increase, particularly for shorter measurement wavelengths. However, by extending the range of wavelengths to 2200 nanometers and larger, successful measurements can be achieved.

In another further aspect, the dimensions of illumination field stop projected on wafer plane are adjusted to optimize the resulting measurement accuracy and speed based on the nature of target under measurement.

In another further aspect, the dimensions of illumination field stop are adjusted to achieve the desired spectral resolution for each measurement application.

In some examples, e.g., if the sample is a very thick film or grating structure, the illumination field stop projected on wafer plane in the direction perpendicular to the plane of incidence is adjusted to reduce the field size to achieve increase spectral resolution. In some examples, e.g., if the sample is a thin film, the illumination field stop projected on wafer plane in the direction perpendicular to the plane of incidence is adjusted to increase the field size to achieve a shortened measurement time without losing spectral resolution.

In the embodiment depicted in FIG. 6, computing system 130 is configured to receive signals 154 indicative of the spectral response detected by the detector subsystem. Computing system 130 is further configured to determine control signals 119 that are communicated to programmable illumination field stop 113. Programmable illumination field stop 113 receives control signals 119 and adjusts the size of the illumination aperture to achieve the desired illumination field size.

In some examples, the illumination field stop is adjusted to optimize measurement accuracy and speed as described hereinbefore. In another example, the illumination field stop is adjusted to prevent image clipping by the spectrometer slit and corresponding degradation of measurement results. In this manner, the illumination field size is adjusted such that the image of the measurement target underfills the spectrometer slit. In one example, the illumination field stop is adjusted such that the projection of the polarizer slit of the illumination optics underfills the spectrometer slit of the metrology system.

Figure 15:
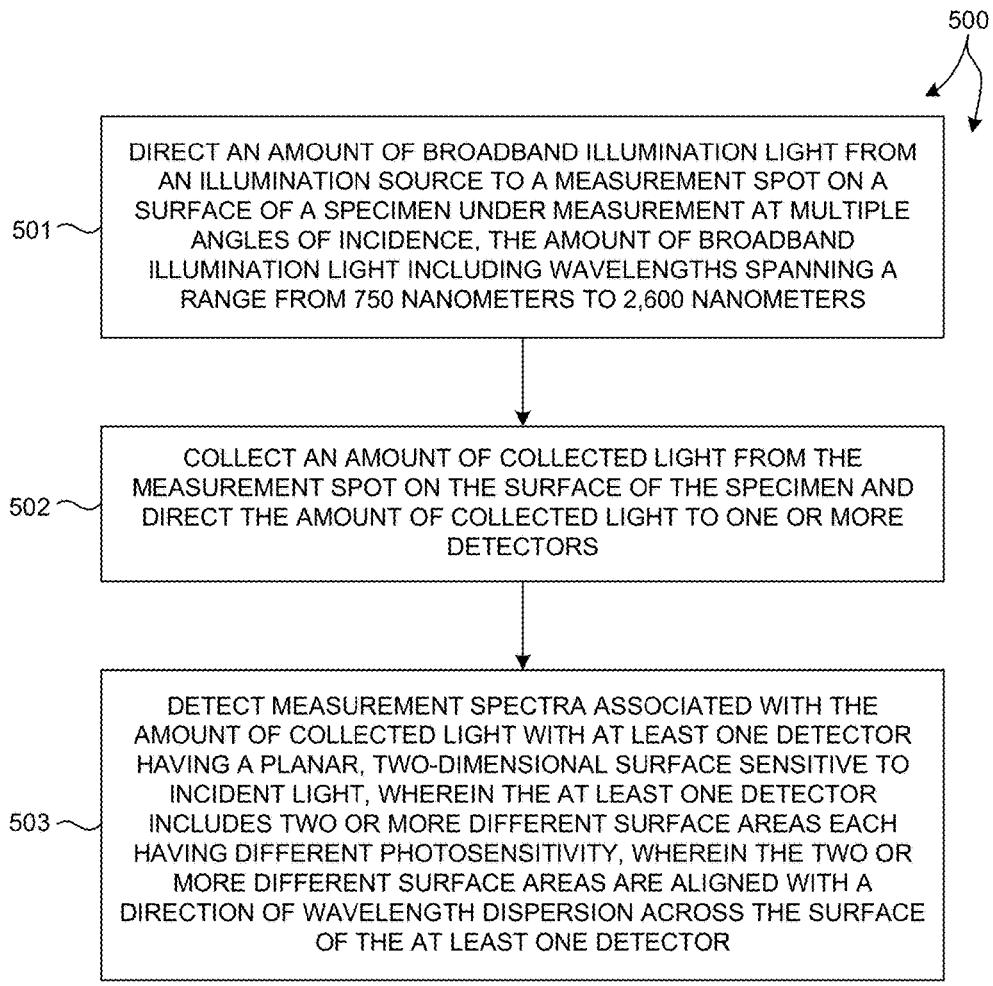
FIG. 15 illustrates a method 500 of performing infrared spectroscopic reflectometry measurements of one or more structures.

FIG. 15 illustrates a method 500 of performing spectroscopic measurements in at least one novel aspect. Method 500 is suitable for implementation by a metrology system such as metrology systems 100, 200, and 300 illustrated in FIGS. 6, 9, and 10, respectively, of the present invention. In one aspect, it is recognized that data processing blocks of method 500 may be carried out via a pre-programmed algorithm executed by one or more processors of computing system 130, or any other general purpose computing system. It is recognized herein that the particular structural aspects of metrology systems 100, 200, and 300 do not represent limitations and should be interpreted as illustrative only.

In block 501, an amount of broadband illumination light is directed from an illumination source to a measurement spot on a surface of a specimen under measurement at multiple angles of incidence. The amount of broadband illumination light includes wavelengths spanning a range from 750 nanometers to 2,600 nanometers.

In block 502, an amount of light is collected from the measurement spot on the surface of the specimen and directed to one or more detectors.

In block 503, measurement spectra associated with the amount of collected light are detected with at least one detector. The at least one detector includes a planar, two-dimensional surface sensitive to incident light having two or more different surface areas each having different photosensitivity. The two or more different surface areas are aligned with a direction of wavelength dispersion across the surface of the at least one detector.

In a further embodiment, systems 100, 200, and 300 include one or more computing systems 130 employed to perform measurements of actual device structures based on spectroscopic measurement data collected in accordance with the methods described herein. The one or more computing systems 130 may be communicatively coupled to the spectrometer. In one aspect, the one or more computing systems 130 are configured to receive measurement data associated with measurements of the structure of the specimen under measurement.

It should be recognized that one or more steps described throughout the present disclosure may be carried out by a single computer system 130 or, alternatively, a multiple computer system 130. Moreover, different subsystems of system 100 may include a computer system suitable for carrying out at least a portion of the steps described herein. Therefore, the aforementioned description should not be interpreted as a limitation on the present invention but merely an illustration.

In addition, the computer system 130 may be communicatively coupled to the spectrometers in any manner known in the art. For example, the one or more computing systems 130 may be coupled to computing systems associated with the spectrometers. In another example, the spectrometers may be controlled directly by a single computer system coupled to computer system 130.

The computer system 130 of metrology system 100 may be configured to receive and/or acquire data or information from the subsystems of the system (e.g., spectrometers and the like) by a transmission medium that may include wireline and/or wireless portions. In this manner, the transmission medium may serve as a data link between the computer system 130 and other subsystems of system 100.

Computer system 130 of metrology system 100 may be configured to receive and/or acquire data or information (e.g., measurement results, modeling inputs, modeling results, reference measurement results, etc.) from other systems by a transmission medium that may include wireline and/or wireless portions. In this manner, the transmission medium may serve as a data link between the computer system 130 and other systems (e.g., memory on-board metrology system 100, external memory, or other external systems). For example, the computing system 130 may be configured to receive measurement data from a storage medium (i.e., memory 132 or an external memory) via a data link. For instance, spectral results obtained using the spectrometers described herein may be stored in a permanent or semi-permanent memory device (e.g., memory 132 or an external memory). In this regard, the spectral results may be imported from on-board memory or from an external memory system. Moreover, the computer system 130 may send data to other systems via a transmission medium. For instance, a measurement model or an estimated parameter value 171 determined by computer system 130 may be communicated and stored in an external memory. In this regard, measurement results may be exported to another system.

Computing system 130 may include, but is not limited to, a personal computer system, mainframe computer system, workstation, image computer, parallel processor, or any other device known in the art. In general, the term "computing system" may be broadly defined to encompass any device having one or more processors, which execute instructions from a memory medium.

Program instructions 134 implementing methods such as those described herein may be transmitted over a transmission medium such as a wire, cable, or wireless transmission link. For example, as illustrated in FIG. 1, program instructions 134 stored in memory 132 are transmitted to processor 131 over bus 133. Program instructions 134 are stored in a computer readable medium (e.g., memory 132). Exemplary computer-readable media include read-only memory, a random access memory, a magnetic or optical disk, or a magnetic tape.

In some examples, the measurement models are implemented as an element of a SpectraShape® optical critical-dimension metrology system available from KLA-Tencor Corporation, Milpitas, Calif., USA. In this manner, the model is created and ready for use immediately after the spectra are collected by the system.

In some other examples, the measurement models are implemented off-line, for example, by a computing system implementing AcuShape® software available from KLA-Tencor Corporation, Milpitas, Calif., USA. The resulting, trained model may be incorporated as an element of an AcuShape® library that is accessible by a metrology system performing measurements.

Figure 14:
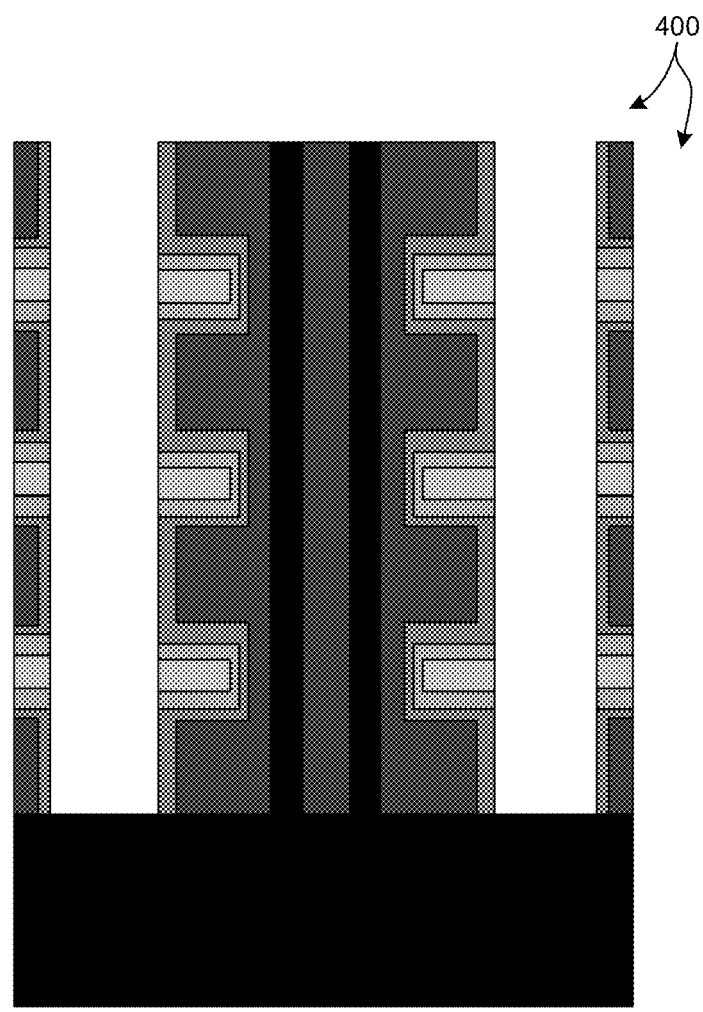
FIG. 14 depicts an exemplary high aspect ratio NAND structure 400 that suffers from low light penetration into the structure(s) being measured.

In another aspect, the methods and systems for spectroscopic metrology of semiconductor devices described herein are applied to the measurement of high aspect ratio (HAR) structures, large lateral dimension structures, or both. The described embodiments enable optical critical dimension (CD), film, and composition metrology for semiconductor devices including three dimensional NAND structures, such as vertical-NAND (V-NAND) structures, dynamic random access memory structures (DRAM), etc., manufactured by various semiconductor manufacturers such as Samsung Inc. (South Korea), SK Hynix Inc. (South Korea), Toshiba Corporation (Japan), and Micron Technology, Inc. (United States), etc. These complex devices suffer from low light penetration into the structure(s) being measured. FIG. 14 depicts an exemplary high aspect ratio NAND structure 400 that suffers from low light penetration into the structure(s) being measured. A spectroscopic ellipsometer with broadband capability and wide ranges of AOI, azimuth angle, or both, having simultaneous spectral band detection as described herein is suitable for measurements of these high-aspect ratio structures. HAR structures often include hard mask layers to facilitate etch processes for HARs. As described herein, the term "HAR structure" refers to any structure characterized by an aspect ratio that exceeds 2:1 or 10:1, and may be as high as 100:1, or higher.

In yet another aspect, the measurement results described herein can be used to provide active feedback to a process tool (e.g., lithography tool, etch tool, deposition tool, etc.). For example, values of measured parameters determined based on measurement methods described herein can be communicated to a lithography tool to adjust the lithography system to achieve a desired output. In a similar way etch parameters (e.g., etch time, diffusivity, etc.) or deposition parameters (e.g., time, concentration, etc.) may be included in a measurement model to provide active feedback to etch tools or deposition tools, respectively. In some example, corrections to process parameters determined based on measured device parameter values and a trained measurement model may be communicated to a lithography tool, etch tool, or deposition tool.

As described herein, the term "critical dimension" includes any critical dimension of a structure (e.g., bottom critical dimension, middle critical dimension, top critical dimension, sidewall angle, grating height, etc.), a critical dimension between any two or more structures (e.g., distance between two structures), and a displacement between two or more structures (e.g., overlay displacement between overlaying grating structures, etc.). Structures may include three dimensional structures, patterned structures, overlay structures, etc.

As described herein, the term "critical dimension application" or "critical dimension measurement application" includes any critical dimension measurement.

As described herein, the term "metrology system" includes any system employed at least in part to characterize a specimen in any aspect, including measurement applications such as critical dimension metrology, overlay metrology, focus/dosage metrology, and composition metrology. However, such terms of art do not limit the scope of the term "metrology system" as described herein. In addition, the metrology system 100 may be configured for measurement of patterned wafers and/or unpatterned wafers. The metrology system may be configured as a LED inspection tool, edge inspection tool, backside inspection tool, macro-inspection tool, or multi-mode inspection tool (involving data from one or more platforms simultaneously), and any other metrology or inspection tool that benefits from the calibration of system parameters based on critical dimension data.

Various embodiments are described herein for a semiconductor measurement system that may be used for measuring a specimen within any semiconductor processing tool (e.g., an inspection system or a lithography system). The term "specimen" is used herein to refer to a wafer, a reticle, or any other sample that may be processed (e.g., printed or inspected for defects) by means known in the art.

As used herein, the term "wafer" generally refers to substrates formed of a semiconductor or non-semiconductor material. Examples include, but are not limited to, monocrystalline silicon, gallium arsenide, and indium phosphide. Such substrates may be commonly found and/or processed in semiconductor fabrication facilities. In some cases, a wafer may include only the substrate (i.e., bare wafer). Alternatively, a wafer may include one or more layers of different materials formed upon a substrate. One or more layers formed on a wafer may be "patterned" or "unpatterned." For example, a wafer may include a plurality of dies having repeatable pattern features.

A "reticle" may be a reticle at any stage of a reticle fabrication process, or a completed reticle that may or may not be released for use in a semiconductor fabrication facility. A reticle, or a "mask," is generally defined as a substantially transparent substrate having substantially opaque regions formed thereon and configured in a pattern. The substrate may include, for example, a glass material such as amorphous $SiO_2$. A reticle may be disposed above a resist-covered wafer during an exposure step of a lithography process such that the pattern on the reticle may be transferred to the resist.

One or more layers formed on a wafer may be patterned or unpatterned. For example, a wafer may include a plurality of dies, each having repeatable pattern features. Formation and processing of such layers of material may ultimately result in completed devices. Many different types of devices may be formed on a wafer, and the term wafer as used herein is intended to encompass a wafer on which any type of device known in the art is being fabricated.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

Although certain specific embodiments are described above for instructional purposes, the teachings of this patent document have general applicability and are not limited to the specific embodiments described above. Accordingly, various modifications, adaptations, and combinations of various features of the described embodiments can be practiced without departing from the scope of the invention as set forth in the claims.

What is claimed is:

1. A metrology system comprising:
    an infrared spectroscopic reflectometer including:
        one or more illumination sources configured to generate an amount of broadband illumination light including wavelengths spanning a range from 750 nanometers to 2,600 nanometers;
        an illumination optics subsystem configured to direct the amount of illumination light from the illumination source to a measurement spot on a surface of a specimen under measurement at one or more angles of incidence, one or more azimuth angles, or a combination thereof;
        a collection optics subsystem configured to collect an amount of collected light from the measurement spot on the surface of the specimen;
        at least one detector having a planar, two-dimensional surface sensitive to incident light, wherein the at least one detector includes two or more different surface areas each having different photosensitivity, wherein the two or more different surface areas are aligned with a direction of wavelength dispersion across the surface of the at least one detector, the at least one detector configured to detect the incident light and generate output indicative of the detected incident light; and
    a computing system configured to generate an estimated value of a parameter of interest of the specimen under measurement based on an analysis of the output of the at least one detector.

2. The metrology system of claim 1, wherein the illumination optics subsystem directs the amount of illumination light to the measurement spot at a plurality of angles of incidence within a range of 5 degrees and 40 degrees.

3. The metrology system of claim 1, further comprising:
    an ultraviolet to near infrared spectroscopic reflectometer configured to measure the specimen with illumination light including wavelengths spanning a range from 190 nanometers to 900 nanometers.

4. The metrology system of claim 1, further comprising:
    a vacuum ultraviolet to ultraviolet spectroscopic reflectometer configured to measure the specimen with illumination light including wavelengths spanning a range from 150 nanometers to 300 nanometers.

5. The metrology system of claim 2, further comprising:
    an infrared spectroscopic ellipsometer configured to measure the specimen with illumination light including wavelengths spanning a range from 750 nanometers to 2600 nanometers.

6. The metrology system of claim 5, further comprising:
    an ultraviolet to near infrared spectroscopic ellipsometer configured to measure the specimen with illumination light including wavelengths spanning a range from 190 nanometers to 900 nanometers.

7. The metrology system of claim 5, further comprising:
    a vacuum ultraviolet to ultraviolet spectroscopic ellipsometer configured to measure the specimen with illumination light including wavelengths spanning a range from 150 nanometers to 300 nanometers.

8. The metrology system of claim 5, wherein the spectroscopic ellipsometer is configured to illuminate the specimen at a plurality of angles of incidence that are greater than 40 degrees.

9. The metrology system of claim 5, wherein the infrared spectroscopic reflectometer and the spectroscopic ellipsometer combined are sensitive to spectral regions over a wavelength range from 150 nanometers to 4,500 nanometers.

10. The metrology system of claim 5, wherein the measurement spot of the infrared spectroscopic reflectometer on the specimen and a measurement spot of the spectroscopic ellipsometer on the specimen are co-located.

11. The metrology system of claim 1, wherein the two or more different surface areas each having different photosensitivity include an InGaAs material.

12. The metrology system of claim 1, further comprising:
    a central obscuration disposed at or near a collection pupil of the collection optics subsystem configured to obscure reflections from a back surface of a substrate of the specimen.

13. The metrology system of claim 1, further comprising:
a central obscuration disposed at or near an illumination pupil of the illumination optics subsystem configured to obscure reflections from a back surface of a substrate of the specimen.

14. The metrology system of claim 1, wherein the one or more angles of incidence does not include a normal angle of incidence.

15. The metrology system of claim 1, wherein an objective of the infrared spectroscopic reflectometer is a Schwartzchild objective.

16. The metrology system of claim 1, wherein the illumination optics subsystem directs the amount of illumination light to the measurement spot at a plurality of angles of incidence within a range of 5 degrees and 25 degrees.

17. The metrology system of claim 1, wherein a measurement channel of the infrared spectroscopic reflectometer includes a polarizing element in an illumination path, a collection path, or both, of the infrared spectroscopic reflectometer.

18. The metrology system of claim 1, wherein the specimen under measurement includes a three dimensional NAND structure or a dynamic random access memory structure.

19. A metrology system comprising:
an infrared spectroscopic reflectometer including:
one or more illumination sources configured to generate an amount of broadband illumination light including wavelengths spanning a range from 750 nanometers to 2,600 nanometers;
an illumination optics subsystem configured to direct the amount of illumination light from the illumination source to a measurement spot on a surface of a specimen under measurement at one or more angles of incidence greater than 5 degrees;
a collection optics subsystem configured to collect an amount of collected light from the measurement spot on the surface of the specimen;
at least one detector having a planar, two-dimensional surface sensitive to incident light, the at least one detector configured to detect the incident light and generate output indicative of the detected incident light; and
a computing system configured to generate an estimated value of a parameter of interest of the specimen under measurement based on an analysis of the output of the at least one detector.

20. The metrology system of claim 19, wherein the at least one detector includes two or more different surface areas each having different photosensitivity, wherein the two or more different surface areas are aligned with a direction of wavelength dispersion across the surface of the at least one detector.

21. The metrology system of claim 20, wherein the two or more different surface areas each having different photosensitivity include an InGaAs material.

22. The metrology system of claim 19, wherein an objective of the infrared spectroscopic reflectometer is a Schwartzchild objective.

23. The metrology system of claim 19, wherein a measurement channel of the infrared spectroscopic reflectometer includes a polarizing element in an illumination path, a collection path, or both, of the infrared spectroscopic reflectometer.

24. A metrology system comprising:
an infrared spectroscopic reflectometer including:
one or more illumination sources configured to generate an amount of broadband illumination light;
an illumination optics subsystem configured to direct the amount of illumination light from the illumination source to a measurement spot on a surface of a specimen under measurement at one or more angles of incidence within a range of 5 degrees and 40 degrees;
a collection optics subsystem configured to collect an amount of collected light from the measurement spot on the surface of the specimen;
at least one detector having a planar, two-dimensional surface sensitive to incident light, wherein the at least one detector includes two or more different surface areas each having different photosensitivity, wherein the two or more different surface areas are aligned with a direction of wavelength dispersion across the surface of the at least one detector, the at least one detector configured to detect the incident light and generate output indicative of the detected incident light; and
a computing system configured to generate an estimated value of a parameter of interest of the specimen under measurement based on an analysis of the output of the at least one detector.

25. The metrology system of claim 24, wherein the amount of broadband illumination light includes wavelengths spanning a range from 750 nanometers to 2,600 nanometers.

26. The metrology system of claim 24, wherein the specimen under measurement includes a three dimensional NAND structure or a dynamic random access memory structure.

27. A method comprising:
directing an amount of broadband illumination light from an illumination source to a measurement spot on a surface of a specimen under measurement at multiple angles of incidence, the amount of broadband illumination light including wavelengths spanning a range from 750 nanometers to 2,600 nanometers;
collecting an amount of collected light from the measurement spot on the surface of the specimen and directing the amount of collected light to one or more detectors; and
detecting measurement spectra associated with the amount of collected light with at least one detector having a planar, two-dimensional surface sensitive to incident light, wherein the at least one detector includes two or more different surface areas each having different photosensitivity, wherein the two or more different surface areas are aligned with a direction of wavelength dispersion across the surface of the at least one detector.

28. The method of claim 27, wherein the detecting of the measurement spectra across the range of illumination wavelengths is performed simultaneously.

* * * * *